United States Patent
Bachmann et al.

(10) Patent No.: US 8,642,802 B2
(45) Date of Patent: *Feb. 4, 2014

(54) PROCESS FOR THE PREPARATION OF HALOGENATED BENZOIC ACID DERIVATIVES

(75) Inventors: Stephan Bachmann, Allschwil (CH); Stefan Hildbrand, Gelterkinden (CH); James Jappy, Surry (GB); Dinesh Maganbhai Patel, Berkshire (GB); Christophe Pfleger, Mulhouse (FR); Robert John Ernest Tidswell, Surry (GB); Rene Trussardi, Birsfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/606,052

(22) Filed: Sep. 7, 2012

(65) Prior Publication Data

US 2012/0330055 A1    Dec. 27, 2012

Related U.S. Application Data

(60) Continuation of application No. 13/365,353, filed on Feb. 3, 2012, now Pat. No. 8,329,939, which is a division of application No. 12/474,434, filed on May 29, 2009, now abandoned.

(30) Foreign Application Priority Data

Jun. 6, 2008 (EP) ..................................... 08157757

(51) Int. Cl.
C07C 51/16    (2006.01)

(52) U.S. Cl.
USPC ........................................................ 562/418

(58) Field of Classification Search
None
See application file for complete search history.

(56) References Cited

U.S. PATENT DOCUMENTS

| 3,823,134 | A | 7/1974 | Houlihan |
| 4,469,893 | A | 9/1984 | Tang et al. |
| 5,196,593 | A | 3/1993 | Seper et al. |
| 5,493,048 | A | 2/1996 | Marhold et al. |
| 5,977,414 | A | 11/1999 | Okabe et al. |
| 6,156,922 | A | 12/2000 | Russell et al. |
| 8,329,939 | B2 * | 12/2012 | Bachmann et al. ........... 562/418 |
| 2003/0092930 | A1 | 5/2003 | Schmidt et al. |

FOREIGN PATENT DOCUMENTS

| DE | 3935934 | 5/1990 |
| EP | 0 491 326 | 6/1992 |
| WO | 97/24318 | 7/1997 |
| WO | 99/35117 | 7/1999 |
| WO | 99/57123 | 11/1999 |

OTHER PUBLICATIONS

Masson et al., *European Journal of Organic Chemistry* (Examiner cited), 20:4393-4400 (2005).
The English translation of the Japanese Office Action, issued on Jul. 23, 2013, in the corresponding Japanese application No. 2011-512078., pp. 5.

* cited by examiner

*Primary Examiner* — Yevegeny Valenrod

(57) ABSTRACT

The present invention comprises a process for the preparation of 3-chloro-2-fluoro-5-trifluoromethyl benzoic acid of the formula

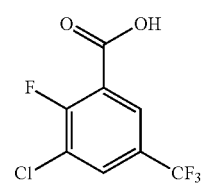

I or of a salt thereof 3-Chloro-2-fluoro-5-trifluoromethyl benzoic acid or salts thereof are versatile intermediates for the preparation of active pharmaceutical or agrochemical agents.

8 Claims, No Drawings

PROCESS FOR THE PREPARATION OF HALOGENATED BENZOIC ACID DERIVATIVES

PRIORITY TO RELATED APPLICATION(S)

This application is a continuation of U.S. application Ser. No. 13/365,353, filed Feb. 3, 2012, which is a divisional application of U.S. application Ser. No. 12/474,434, filed May 29, 2009, now pending, which claims the benefit of European Patent Application No. 08157757.9, filed Jun. 6, 2008. The entire contents of the above-identified applications are hereby incorporated by reference.

FIELD OF THE INVENTION

The invention is directed generally to processes for the preparation of 3-chloro-2-fluoro-5-trifluoromethyl benzoic acids and salts thereof and more particularly comprises a process for the preparation of 3-chloro-2-fluoro-5-trifluoromethyl benzoic acid of the formula

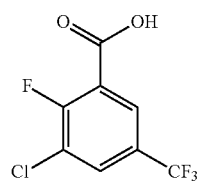

I or of a salt thereof.

BACKGROUND OF THE INVENTION

Certain art, e.g., DE A13935934 discloses a preparation of 3-chloro-2-fluoro-5-trifluoromethyl-benzoic acid which comprises the conversion of 1,3-dichloro-2-fluoro-(trifluoromethyl)benzene with tert-butyl lithium/pentane and subsequent carbon dioxide treatment. However, this preparation process suffers from the use of corrosive chemicals at low temperatures of −78° C. and thus creates a scaling issue.

Accordingly, it would be advantageous to develop a process for the preparation of 3-chloro-2-fluoro-5-trifluoromethyl-benzoic acid compounds which could be performed on technical scale and overcome or avoid such known drawbacks in the art.

SUMMARY OF THE INVENTION

The process for the preparation of 3-chloro-2-fluoro-5-trifluoromethyl benzoic acid of the formula

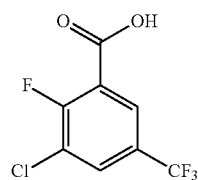

I or of a salt thereof comprises the conversion of 3-chloro-4-fluoro-benzo trifluoride of the formula

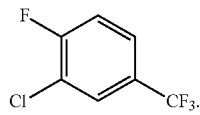

II

The 3-chloro-4-fluoro-benzo trifluoride starting compound is commercially available or can be prepared according to U.S. Pat. No. 4,469,893 (1984) or WO1997024318 (1997).

In a further embodiment of the present invention the conversion is performed by either $a_1$) deprotonating the 3-chloro-4-fluoro-benzo trifluoride with a metalorganic base followed by adding $CO_2$ as electrophile in an organic solvent at a reaction temperature of −100° C. to 25° C.

or $b_1$) by forming a Grignard compound of the 3-chloro-4-fluoro-benzo trifluoride with an alkyl or an aryl magnesium halide in an organic solvent at a reaction temperature of 20° C. to 100° C. followed by adding $CO_2$ as electrophile in an organic solvent at a reaction temperature of −100° C. to 25° C.

DETAILED DESCRIPTION

The following definitions are set forth to illustrate and define the meaning and scope of the various terms used to describe the invention herein. All references cited herein are hereby incorporated by reference in their entirety.

The term "alkyl" relates to a branched or straight-chain monovalent saturated aliphatic hydrocarbon radical of one to six carbon atoms, preferably one to four carbon atoms. This term is further exemplified by radicals as methyl, ethyl, n-propyl, isopropyl, n-butyl, s-butyl, t-butyl and pentyl or hexyl and its isomers.

The term "aryl" relates to the phenyl or naphthyl group, preferably the phenyl group, which can optionally be mono-, di-, tri- or multiply-substituted by halogen, hydroxy, CN, halogen-$C_{1-6}$-alkyl, $NO_2$, $NH_2$, N(H, alkyl), N(alkyl)$_2$, carboxy, aminocarbonyl, alkyl, alkoxy, alkylcarbonyl, $C_{1-6}$-alkylsulfonyl, $SO_2$-aryl, $SO_3H$, $SO_3$-alkyl, $SO_2$—NR'R", aryl and/or aryloxy. Preferred aryl group is phenyl.

Step $a_1$)

Suitable metalorganic bases for the deprotonation in step a) can be selected from lithium bases such as n-butyl lithium, s-butyl lithium, t-butyl lithium or alkalimetal-amines. More preferred is n-butyl lithium or lithium diisopropylamide, even more preferred n-butyl lithium. The term "alkalimetal-amine", refers to a secondary amine substituted by an alkali metal as defined herein. The "alkalimetal-amine" is either prepared in situ or ex situ prior to use, following synthetic routes well known by the person skilled in the art or it is available commercially. The most preferred alkali metal to be used is lithium. Exemplary alkalimetal-amine includes lithium adducts of dicyclohexyl amine, diisopropyl amine, tetramethyl piperidine or hexamethyl disilazane. The most preferred alkalimetal-lithium is lithium diisopropyl amine. The term "alkali metal" includes lithium, sodium and potassium. Preferable alkali metal is lithium or sodium.

"Secondary amine" refers to an amine of formula (a)

where $R^a$ and $R^b$ may be the same or different and are independently selected from $(C_1$-$C_6)$ alkyl, $(C_3$-$C_6)$ cycloalkyl or —Si$(C_1$-$C_6)$ alkyl, or $R^a$ and $R^b$ taken together with the nitrogen atom to which they are attached, form a $(C_4$-$C_8)$heterocycloalkane optionally containing an additional heteroatom selected from O or N. Representative examples include, but are not limited to, piperidine, 4-methyl-piperidine, piperazine, pyrrolidine, morpholine, dimethylamine, diethylamine, diisopropylamine, dicyclohexylamine, ethylmethylamine, ethylpropylamine, methylpropylamine and hexamethyl disilazide. Preferably, the secondary amine is chosen from diethylamine, diisopropylamine, dicyclohexylamine, ethylmethylamine, ethylpropylamine and methylpropylamine.

The metalorganic base can be used in an amount of 0.9 to 2.0 equivalents, preferably 1.0 to 1.5 equivalents and even more preferred in an amount of 1.0 to 1.1 equivalents related to the starting compound 3-chloro-4-fluoro-benzo trifluoride.

The deprotonation as a rule is performed in a suitable organic solvent, preferably in an ether such as in tetrahydrofuran, 2-methyltetrahydrofuran, methoxycyclopentane, diethyl ether t-butyl methyl ether, or dioxane or in a combination of ethers with hydrocarbons such as toluene, pentane, hexane, cyclohexane or methyl cyclohexane, but preferably in tetrahydrofuran, 2-methyltetrahydrofuran or tetrahydrofuran/hexane.

The reaction temperature for the deprotonation is selected between −100° C. and 25° C., preferably between −78° C. and −50° C., even more preferred between −70° C. and −78° C.

The subsequent reaction with $CO_2$ can happen by slowly adding the reaction mixture to a solution of $CO_2$ in an organic solvent, which as a rule is the same solvent as for the deprotonation reaction. The reaction temperature is kept in the same range as outlined above for the deprotonation reaction.

Upon completion of the reaction the target product can be isolated after acidifying the reaction mixture upon the addition of a protic acid and/or water and after extraction from the aqueous phase with a suitable organic solvent such as with t-butyl methyl ether.

Protic acid refers to Brønsted acid that donates at least one proton (H+) to another compound. Typical protic acids include aqueous mineral acids such as nitric acid, sulfuric acid, phosphoric acid, hydrogen halides acid, organic acids such as methanesulfonic acid, benzenesulfonic acid, acetic acid, citric acid and the like and complex acids such as tetrafluoro boronic acid, hexafluoro phosphoric acid, hexafluoro antimonic acid and hexafluoro arsenic acid. Preferred protic acids are citric acid, acetic acid and HCl.

Step $b_1$)

The formation of the Grignard compound is usually performed with an alkyl or aryl magnesium halide, preferably in the presence of an amine base, preferably a secondary amine applying a reaction temperature of 20° C. to 100° C., preferably 20° C. to 60° C.

Suitable secondary amines have been listed under step $a_1$. Preferred secondary amine is diisopropylamine.

Representative examples of alkyl or aryl magnesium halides include, but are not limited to, ethyl magnesium bromide, methyl magnesium bromide, methyl magnesium chloride, methyl magnesium iodide, propyl magnesium chloride, iso-propyl magnesium chloride, sec-butyl magnesium chloride, sec-butyl magnesium chloride, tert-butyl magnesium chloride, allyl magnesium chloride, allyl magnesium bromide, vinyl magnesium bromide, cyclopentyl magnesium chloride, hexyl magnesium chloride, benzyl magnesium chloride, phenyl magnesium bromide, phenyl magnesium chloride, p-toluoyl magnesium bromide, mesyl magnesium bromide. Preferred alkyl magnesium halide is ethyl magnesium bromide.

The same solvents as suggested for the deprotonation may be used for the formation of the Grignard compound. Preferred solvent is tetrahydrofuran.

The subsequent reaction with $CO_2$ can happen by slowly adding the reaction mixture to a solution of $CO_2$ in an organic solvent, which as a rule is the same solvent as for the deprotonation reaction.

The reaction temperature is selected between −100° C. and 25° C., preferably between −78° C. and −50° C., even more preferred between −70° C. and −78° C.

Upon completion of the reaction the target product can be isolated after acidifying the reaction mixture with a protic acid (e.g. aqueous HCl) and/or water and after extraction from the aqueous phase with a suitable organic solvent such as with t-butyl methyl ether.

In a further embodiment of the present invention the conversion is performed by $a_2$) transforming the 3-chloro-4-fluoro-benzo trifluoride of formula II into the 3-chloro-2-fluoro-5-trifluoromethyl benzaldehyde of the formula

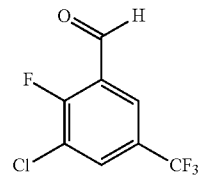

III and $b_2$) oxidizing the 3-chloro-2-fluoro-5-trifluoromethyl benzaldehyde with an oxidant to form the 3-chloro-2-fluoro-5-trifluoromethyl benzoic acid of formula I or of a salt thereof.

Step $a_2$)

The transformation into the 3-chloro-2-fluoro-5-trifluoromethyl benzaldehyde of the formula III is usually performed by deprotonating the 3-chloro-4-fluoro-benzo trifluoride with a metalorganic base followed by adding an electrophile selected from an N,N-dialkylformamide, an N,N-diarylformamide or N-alkoxy-N-alkyl formamides in an organic solvent at a reaction temperature of −100° C. to 25° C.

The deprotonation can be performed as outlined above for step $a_1$.

The addition of the electrophile as a rule can happen at the same temperature and in the same solvent as described for the deprotonation reaction. Usually the electrophile is added in an amount of 0.9 to 5.0 equivalents, preferably 1.0 to 1.5 equivalents, even more preferred 1.0 to 1.1 equivalents relating to 1.0 equivalent of the starting compound.

Representative examples of N,N-dialkylformamides or N,N-diarylformamides include, but are not limited to, N,N-diphenylformamide, N-Methylformanilide, N,N-diethylformamide, N,N-dibutylformamide, 1-Formylpiperazine, 1,4-diformylpiperazine, N-Methylmorpholine, N-Methyl-N-(2-pyridyl)-formamide, N-Methylpiperidine, N,N- diisopropylformamide, 2-Methoxy-1-formyl-piperidine, N,N-diallylformamide, N,N-di-n-propyl-formamide, N,N-dibenzylformamide, 1-formyl-pyrrolidine.

Representative examples of N-alkoxy-N-alkyl formamides include, but are not limited to, N-methoxy-N-methyl formamide, N-benzyloxy-N-methyl formamide or N-ethoxy-N-methyl formamide. Preferred electrophile is N,N-dimethylformamide.

Usually a protic acid as quenching agent is added subsequent to the deprotonation and subsequent to the addition of the electrophile.

Protic acid refers to Brønsted acid that donates at least one proton (H+) to another compound. Typical protic acids include aqueous mineral acids such as nitric acid, sulfuric acid, phosphoric acid, hydrogen halides acid, organic acids such as methanesulfonic acid, benzenesulfonic acid, acetic acid, citric acid and the like and complex acids such as tetrafluoro boronic acid, hexafluoro phosphoric acid, hexafluoro antimonic acid and hexafluoro arsenic acid. Preferred protic acids are citric acid, acetic acid and sulfuric acid.

Quenching is as a rule performed at a temperature of –78° C. to 25° C.

The 3-chloro-2-fluoro-5-trifluoromethyl benzaldehyde of the formula III can be isolated using methods known to the skilled in the art e.g. by way of extraction from the aqueous phase with a suitable organic solvent such as with t-butyl methyl ether $CH_2Cl_2$ or toluene and subsequent removal of the solvent.

In a preferred embodiment the 3-chloro-2-fluoro-5-trifluoromethyl benzaldehyde of the formula III is extracted from the aqueous reaction mixture with toluene. The concentrated toluene phase can then, without isolating the aldehyde, be used for the oxidation in step $b_2$).

Step $b_2$)

The oxidant is selected from a compound which is able to transfer oxygen atoms such as from alkali- or alkali earth hypochlorites, -hypobromites, -chlorites, -chlorates, -persulfates or -permanganates. Common representatives are sodium hypochlorite, calcium hypochlorite, sodium chlorate, calcium chlorate, potassium peroxymonosulfate (Oxone®) or potassium permanganate. Preferably sodium hypochlorite or sodium or potassium hypobromite may be used, whereby the latter two can be produced in situ by adding bromine to an aqueous solution of sodium or potassium hydroxide or by adding sodium or potassium bromide to an aqueous basic solution of sodium hypochlorite. Most preferred oxidant is sodium hypochlorite in combination with potassium bromide.

In a further preferred embodiment the reaction is performed in the presence of an aqueous alkali hydroxide base, preferably sodium hydroxide or potassium hydroxide, even more preferred in the presence of sodium hydroxide.

An additive selected from an alkali bromide and/or from TEMPO (2,2,6,6-Tetramethylpiperidinyloxy) can be used, whereby sodium bromide or potassium bromide are preferred and potassium bromide is the most preferred additive.

The oxidation can be performed in an aqueous solvent selected from water and mixtures thereof with a suitable organic solvent such as with N,N-dimethylformamide, dimethyl acetamide, acetonitrile, toluene, $CH_2Cl_2$ or with mixtures of these organic solvents. Preferably the oxidation is performed in water or in a mixture of water and toluene.

A quenching agent, e.g. aqueous sodium sulfite may be added subsequent to the oxidation reaction.

The reaction temperature as a rule is chosen between 10° C. to 100° C., preferably between 10° C. and 60° C., more preferably at 20° C. to 50° C.

The isolation of the 3-chloro-2-fluoro-5-trifluoromethyl benzoic acid of formula I can preferably happen by separating off organic impurities from the reaction mixture (set at a pH of >11) with toluene, by acidifying the product containing aqueous phase to a pH<2 and by extracting the product from the aqueous phase with toluene.

In a preferred embodiment of the invention the isolated product can further be purified by crystallization with cyclohexane, heptane, methyl cyclohexane or mixtures thereof.

In a further embodiment of the present invention the conversion is performed by $a_3$) converting the 3-chloro-4-fluoro-benzo trifluoride of formula II into an alkali (3-chloro-2-fluoro-5-trifluoromethyl-phenyl)-hydroxy-methanesulfonate of formula

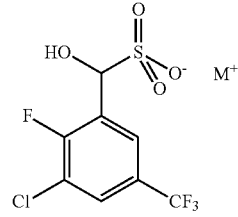

IV wherein M is an alkali metal atom;

$b_3$) transforming the alkali (3-chloro-2-fluoro-5-trifluoromethyl-phenyl)-hydroxy-methanesulfonate of formula IV into the 3-chloro-2-fluoro-5-trifluoromethyl benzaldehyde of the formula

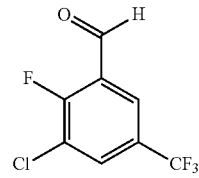

III and $c_3$) oxidizing the 3-chloro-2-fluoro-5-trifluoromethyl benzaldehyde of formula III with an oxidant to form the 3-chloro-2-fluoro-5-trifluoromethyl benzoic acid of formula I or of a salt thereof.

Step $a_3$

Step $a_3$ involves the conversion of the 3-chloro-4-fluoro-benzo-trifluoride of formula II into an alkali (3-chloro-2-fluoro-5-trifluoromethyl-phenyl)-hydroxy-methane-sulfonate of formula IV by $a_4$) deprotonating the 3-chloro-4-fluoro-benzo trifluoride with a metalorganic base followed by $b_4$) adding an electrophile selected from an N,N-dialkylformamide, an N,N-diarylformamide or N-alkoxy-N-alkyl formamides, in an organic solvent at a reaction temperature of –100° C. to 25° C., by $c_4$) adding a protic acid as quenching agent and finally by $d_4$) forming the alkali (3-chloro-2-fluoro-5-trifluoromethyl-phenyl)-hydroxy-methanesulfonate of formula IV with an alkali pyrosulfite or an aqueous solution of a alkali hydrogen sulfite.

The deprotonation step, the addition of the electrophile and the quenching step can be performed as outlined above for step $a_2$.

For the formation of the alkali (3-chloro-2-fluoro-5-trifluoromethyl-phenyl)-hydroxy-methanesulfonate of formula IV in step $d_4$) usually an aqueous solution of sodium pyrosulfite is used. The transformation as a rule is performed in suitable organic solvent such as in toluene, at a reaction temperature of 0° C. to 50° C.

Upon completion of the reaction the product of step $d_4$) can be isolated by filtration from the reaction mixture.

Step $b_3$

The transformation of the alkali (3-chloro-2-fluoro-5-trifluoromethyl-phenyl)-hydroxy-methanesulfonate of formula IV into the 3-chloro-2-fluoro-5-trifluoromethyl benzaldehyde of the formula III is performed with an aqueous alkali hydroxide base, preferably sodium hydroxide or potassium hydroxide, even more preferred with sodium hydroxide.

The transformation as a rule is performed in the presence of a suitable water immiscible organic solvent such as in methylene chloride, toluene or TBME at a reaction temperature of −20° C. to 40° C.

The resulting 3-chloro-2-fluoro-5-trifluoromethyl benzaldehyde of the formula III can be separated from the organic phase by removing the solvent.

Step $c_3$

The oxidation of the 3-chloro-2-fluoro-5-trifluoromethyl benzaldehyde of formula III to the 3-chloro-2-fluoro-5-trifluoromethyl benzoic acid of formula I or of a salt thereof can take place as outlined for the step $b_2$) above.

In a preferred embodiment of the invention the isolated product can further be purified by crystallization with cyclohexane, heptane, methyl cyclohexane or mixtures thereof.

The following examples serve to illustrate the invention in more detail. These examples are not intended to limit the scope of the invention in any manner.

EXAMPLES

Example 1.1

Synthesis of
3-chloro-2-fluoro-5-trifluoromethyl-benzaldehyde

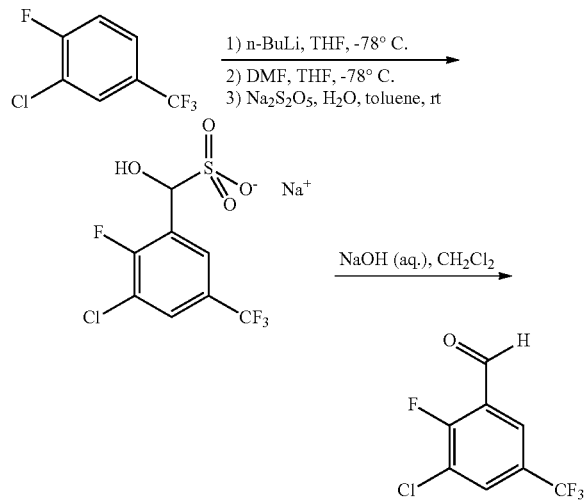

To a solution of 3-Chloro-4-fluoro-benzotrifluoride (59.9 g, 301.7 mmol) in THF (400 ml) was added at −78° C. n-BuLi (135.5 g, 309.7 mmol, 1.03 equiv.) dropwise over a period of ca. 30 min. The clear yellow solution was stirred for 30 min at −78° C. and a solution of DMF (24.5 g, 334.5 mmol, 1.11 equiv.) in THF (107 ml) were added dropwise, such as that the internal temperature stayed below −70° C. The light yellow reaction mixture was stirred for 1 h at −78° C. and was then warmed to 0° C. At this temperature the reaction mixture was quenched upon addition of an aqueous citric acid solution (600 ml, 15%). To this mixture, toluene (300 ml) was added; the organic phase was separated and washed with water (200 ml), whereas the aqueous phase was washed with toluene (300 ml). The combined organic phases were dried over sodium sulfate, and concentrated under vacuum to a volume of ca. 450 ml. To this solution was added a solution of sodium pyrosulfite (66.4 g, 331.8 mmol, 1.10 equiv.) in water (200 ml), whereupon a white precipitate was formed. The white suspension was stirred overnight; the precipitate was filtered off, washed with toluene (200 ml) and dried under vacuum (<50 mbar) for 3 h to yield the bi-sulfite intermediate (110 g, 110% yield). The obtained intermediate was taken up in $CH_2Cl_2$ (350 ml) and treated with NaOH (2M) solution (310 ml, 620 mmol, 2.06 equiv.) and the bi-phasic mixture was stirred for 2 h. The phases were separated, the organic phase was washed with water (200 ml), dried over sodium sulfate and the solvent was removed under vacuum to yield the title compound as colorless oil (52.7 g, 77.1% yield). MS (EI): m/z 225 ([M−H]+, 100%). $^1$H-NMR ($CDCl_3$, 300 MHz): δ 10.38 (s, 1H), 8.07 (dd, 1H), 7.94 (dd, 1H).

Example 1.2

Synthesis of
3-chloro-2-fluoro-5-trifluoromethyl-benzaldehyde

Isolation Via Distillation

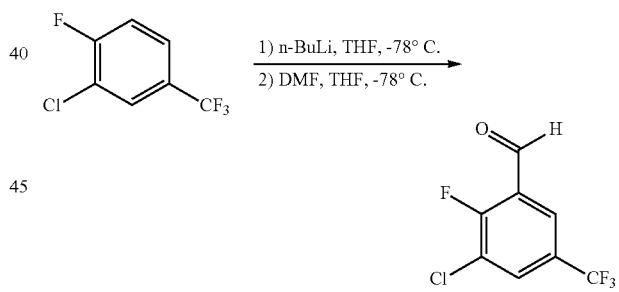

To a solution of 3-Chloro-4-fluoro-benzotrifluoride (5.0 g, 25.18 mmol) in THF (40 ml) was added at −78° C. n-BuLi (16.5 ml, 26.44 mmol, 1.05 equiv.) dropwise over a period of ca. 30 min. The clear yellow solution was stirred for 20 min at −78° C. and was then transferred dropwise via cannula to a pre-cooled (−78° C.) solution of DMF (2.14 ml, 27.7 mmol, 1.1 equiv.) in THF (75 ml) such that the internal temperature stayed below −65° C. The light yellow reaction mixture was stirred for 1 h at −78° C. and was then warmed to 0° C. At this temperature the reaction mixture was quenched upon addition of a solution of citric acid (14.54 g, 75.55 mmol, 3 equiv.) in water (50 ml). The organic phase was separated and washed with water (50 ml), whereas the aqueous phase was washed with TBME (50 ml). The combined organic phases were dried over sodium sulfate, filtered and the solvents were removed under vacuum to yield the crude title compound as yellow oil with a white precipitate (6.8 g, 119.2% yield). The crude product was distilled (Kugelrohr, 110-120° C., 1 mbar) to yield the title compound as colorless oil (4.52 g, 71.9% yield).

Example 2.1

Synthesis of sodium (3-chloro-2-fluoro-5-trifluoromethyl-phenyl)-hydroxy-methanesulfonate Addition of DMF to Li Salt

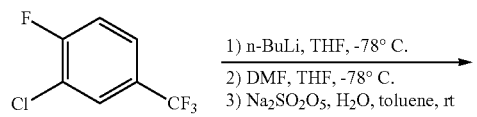

1) n-BuLi, THF, -78° C.
2) DMF, THF, -78° C.
3) Na$_2$SO$_2$O$_5$, H$_2$O, toluene, rt

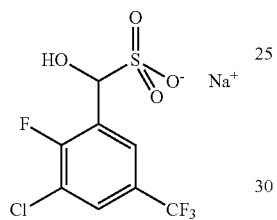

To a solution of 3-Chloro-4-fluoro-benzotrifluoride (20.0 g, 100.7 mmol) in THF (200 ml) was added at −78° C. n-BuLi (1.6 M in hexanes, 66.1 ml, 105.7 mmol, 1.05 equiv.) over a period of ca. 20 min. The clear yellow solution was stirred for 30 min at −78° C. and a solution of DMF (8.54 ml, 110.8 mmol, 1.1 equiv.) in THF (100 ml) was added dropwise, such as that the internal temperature stayed below −70° C. The light yellow reaction mixture was stirred for 3 h at −78° C. and was then warmed to 0° C. At this temperature the reaction mixture was quenched upon addition of a solution of citric acid (58.13 g, 302.1 mmol, 3.0 equiv.) in water (400 ml) keeping the temperature below 5° C. The organic phase was separated and washed with water (300 ml), whereas the aqueous phase was washed with TBME (300 ml). The combined organic phases were dried over sodium sulfate, the solvents were removed under vacuum and the residue was treated with toluene (200 ml), whereupon a white precipitate was formed. The suspension was stirred for 15 min, the precipitate was filtered off and the mother liquor was treated by dropwise addition of a solution of sodium pyrosulfite (21.68 g, 111.8 mmol, 1.11 equiv.) in water (60 ml), whereupon a white suspension was formed. The suspension was stirred overnight (ca. 15 h), the precipitate was filtered off, washed with toluene (100 ml) and dried under vacuum to yield the title compound as a off-white crystalline compound (32.54 g, 97.7% yield).

MS (EI): m/z 306.9 ([M−H]$^-$, 100%). $^1$H-NMR (DMSO, 300 MHz): δ 8.00-7.85 (m, 2H), 6.58 (d, 1H), 5.31 (d, 1H).

Example 2.2

Synthesis of sodium (3-chloro-2-fluoro-5-trifluoromethyl-phenyl)-hydroxy-methanesulfonate Addition of Li Salt to Pre-Cooled DMF Solution

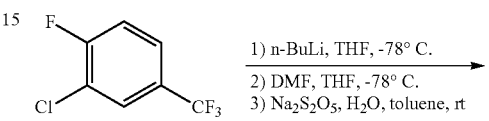

1) n-BuLi, THF, -78° C.
2) DMF, THF, -78° C.
3) Na$_2$S$_2$O$_5$, H$_2$O, toluene, rt

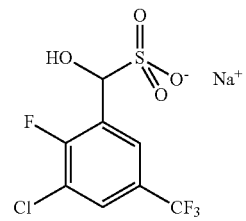

To a solution of 3-Chloro-4-fluoro-benzotrifluoride (5.0 g, 25.18 mmol) in THF (40 ml) was added at −78° C. n-BuLi (1.6 M in hexanes, 16.53 ml, 26.45 mmol, 1.05 equiv.) over a period of ca. 20 min. The clear yellow solution was stirred for 15 min at −78° C. and then transferred dropwise via cannula to a pre-cooled (−78° C.) solution of DMF (2.14 ml, 27.7 mmol, 1.1 equiv.) in THF (100 ml) such as that the internal temperature stayed below −65° C. The light yellow reaction mixture was stirred for 2 h at −78° C., was then warmed to 0° C. and quenched upon addition of a acetic acid (4.32 g, 75.54 mmol, 3.0 equiv.) and water (50 ml) keeping the temperature below 5° C. The turbid light yellow suspension was stirred for 2 h, the precipitate was filtered off with suction on a funnel with a fritted disk and the filter cake was washed with TBME (30 ml). The organic phase was separated and washed with water (50 ml), whereas the aqueous phase was washed with TBME (50 ml). The combined organic phases were dried over sodium sulfate, filtered and the solvents were removed under vacuum and the residue was treated with toluene (40 ml) and a solution of sodium pyrosulfite (5.42 g, 27.95 mmol, 1.11 equiv.) in water (12 ml) was added, whereupon a white suspension was formed. The suspension was stirred overnight (ca. 15 h), the precipitate was filtered off, washed with toluene (20 ml) and dried under vacuum to yield the title compound as a light yellow crystalline compound (7.82 g, 93.9% yield).

Example 3.1

Synthesis of 3-chloro-2-fluoro-5-trifluoromethyl benzoic acid

Oxidation with NaOCl, KBr

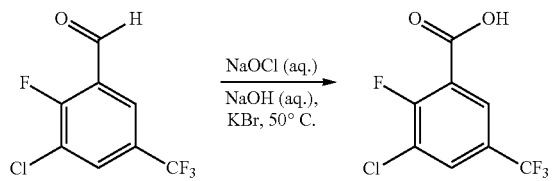 [SMILES: O=Cc1cc(C(F)(F)F)cc(Cl)c1F ; O=C(O)c1cc(C(F)(F)F)cc(Cl)c1F]

To an aqueous solution of sodium hypochlorite (100.3 g, 134.7 mmol, 1.22 equiv.) and potassium bromide (13.5 g, 112.3 mmol, 1.02 equiv.) in sodium hydroxide solution (32%, 34.5 g, 276.0 mmol, 2.50 equiv.) was added slowly (during 35 min) at 50° C. 3-chloro-2-fluoro-5-trifluoromethyl-benzaldehyde (25.0 g, 110.4 mmol). The reaction mixture was stirred at 50° C. for 60 min, cooled to ambient temperature and quenched upon addition of sodium sulfite (60.4 g, 474.5 mmol, 4.3 equiv.) in water (450 ml) to give a clear yellow solution. The solution was treated with HCl (25%, 100 ml, 788.7 mmol, 7.14 equiv.) adjusting the pH to <2. The formed precipitate was extracted with toluene (300 ml), the organic phase was washed with a solution of sodium chloride (5%, 100 ml), dried over sodium sulfate and the solvents were removed under vacuum to give the crude product as light yellow solid. The crude product was dissolved in hot cyclohexane (125 ml), and the solution was cooled to ambient temperature, whereupon white crystals precipitated. The crystals were filtered off, washed with cyclohexane (25 ml) and dried under vacuum until weight constancy to give the title compound as white crystals (23.0 g, 85.8% yield). MS (EI): m/z 241.1 ([M−H]$^-$, 100%). $^1$H-NMR (DMSO, 400 MHz): δ 14.08 (br s, 1H), 8.37-8.35 (dd, 1H), 8.11-8.09 (dd, 1H).

Example 3.2

Synthesis of 3-chloro-2-fluoro-5-trifluoromethyl benzoic acid

Oxidation with NaOCl, NaBr

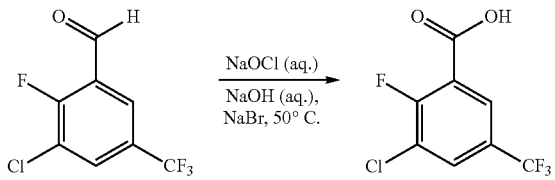 [SMILES: O=Cc1cc(C(F)(F)F)cc(Cl)c1F ; O=C(O)c1cc(C(F)(F)F)cc(Cl)c1F]

To an aqueous solution of sodium hypochlorite (15.3 ml, 25.7 mmol, 1.2 equiv.) and sodium bromide (2.6 g, 25.7 mmol, 1.2 equiv.) in sodium hydroxide solution (47%, 4.55 ml, 53.5 mmol, 2.50 equiv.) and water (12.5 ml) was added slowly (during 25 min) at 50° C. 3-chloro-2-fluoro-5-trifluoromethyl-benzaldehyde (5.0 g, 21.4 mmol). The reaction mixture was stirred at 50° C. for 60 min, cooled to ambient temperature and quenched upon addition of aqueous sodium sulfite solution (20%, 16.2 ml, 25.7 mmol, 1.2 equiv.) to give a light turbid suspension. The suspension was stirred for 15 min, treated with HCl (37%, 5.0 ml, 59.1 mmol, 2.76 equiv.) adjusting the pH to 1, whereupon a white precipitate formed. This precipitate was extracted with toluene (30 ml), the organic phase was washed with brine (30 ml), whereas the aqueous phase was washed with TBME (30 ml). The combined organic phases were dried over sodium sulfate, filtered and the solvent was removed under vacuum to give the crude product as light yellow solid (5.13 g, 98.8% yield). The crude product was dissolved in hot cyclohexane (25 ml), and the solution was cooled to ambient temperature, whereupon white crystals precipitated. The crystals were filtered off, washed with cyclohexane (5 ml) dried under vacuum until weight constancy to give the title compound as white crystals (3.65 g, 69.6% yield).

Example 3.3

Synthesis of 3-chloro-2-fluoro-5-trifluoromethyl benzoic acid

Oxidation with NaOCl/NaBr and 1.5 Equiv NaOH

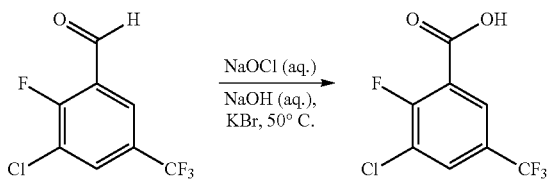 [SMILES: O=Cc1cc(C(F)(F)F)cc(Cl)c1F ; O=C(O)c1cc(C(F)(F)F)cc(Cl)c1F]

To an aqueous solution of sodium hypochlorite (15.3 ml, 25.7 mmol, 1.2 equiv.) and sodium bromide (2.6 g, 25.7 mmol, 1.2 equiv.) in sodium hydroxide solution (47%, 2.73 ml, 32.12 mmol, 1.50 equiv.) and water (12.5 ml) was added slowly (during 25 min) at 50° C. 3-chloro-2-fluoro-5-trifluoromethyl-benzaldehyde (5.0 g, 21.4 mmol). The reaction mixture was stirred at 50° C. for 60 min, cooled to ambient temperature and quenched upon addition of aqueous sodium sulfite solution (20%, 16.2 ml, 25.7 mmol, 1.2 equiv.) to give a light turbid suspension and stirred for 1 h. The suspension was stirred for 15 min, treated with HCl (37%, 4.0 ml, 47.3 mmol, 2.21 equiv.) adjusting the pH to 1, whereupon a white precipitate formed. This precipitate was extracted with TMBE (30 ml), the organic phase was washed with brine (30 ml), whereas the aqueous phase was washed with TBME (30 ml). The combined organic phases were dried over sodium sulfate, filtered and the solvent was removed under vacuum to give the crude product as light yellow solid (5.12 g, 98.6% yield). The crude product was dissolved in hot methylcyclohexane (25 ml), and the solution was cooled to ambient temperature, whereupon white crystals precipitated. The crystals were filtered off with suction on a funnel with a fritted disk, washed with methylcyclohexane (5 ml) dried under vacuum until weight constancy to give the title compound as white crystals (4.27 g, 81.6% yield).

Example 3.4

Synthesis of 3-chloro-2-fluoro-5-trifluoromethyl benzoic acid

Oxidation with Br₂/NaOH (JRD)

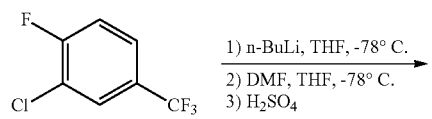

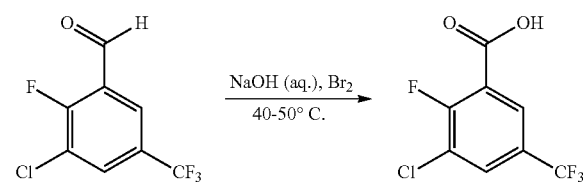

A: A solution of n-BuLi in hexanes (1.6 M, 6.5 l, 10.24 mol, 1.024 equiv.) was added under nitrogen to a stirred solution of 3-chloro-4-fluoro-benzotrifluoride (1.985 kg, 10 mol) in THF (10 l) maintaining the temperature below −50° C. After complete addition of the benzotrifluoride, the resulting reaction mixture was stirred for 15 min at −55° C. and DMF was added in a slow stream. After complete addition, the reaction mixtures was stirred for 15 min and hydrolyzed upon addition of sulfuric acid (20%, 5 l). The organic layer was separated, the THF/hexanes were removed under vacuum and the residual liquid was distilled under vacuum to yield a clear oil. This material was taken through to the benzoic acid without determination of the yield as described in section B.

B: A solution of sodium hypobromite was prepared by adding bromine (1.15 kg, 7.18 mol) to a gently cooled mixture of sodium hydroxide (47%, 1.933 kg) in water (7.735 l). To this solution was added 3-chloro-2-fluoro-5-trifluoromethyl-benzaldehyde (1.50 kg, 6.62 mol) in a stream, whereupon the reaction mixture warmed to about 40-50° C. When the addition was complete, the mixture was stirred for a further 15 min and then acidified with hydrochloric acid (36%), whereupon the product precipitated. The acid was collected by filtration, was pressed as dry as possible on the filter and was then azeotropically dried using petroleum ether (80-100° C.). After removal of the water, the remaining petrol solution was decanted from any inorganic residue and allowed to crystallize. The product was filtered, washed well with petroleum ether (40-60° C.) and dried in a vacuum oven until weight constancy to give the product as white crystals (1.5 kg, 61.8% yield based on 3-chloro-4-fluoro-benzotrifluoride).

Example 3.5

Synthesis of 3-chloro-2-fluoro-5-trifluoromethyl benzoic acid

Oxidation with Oxone

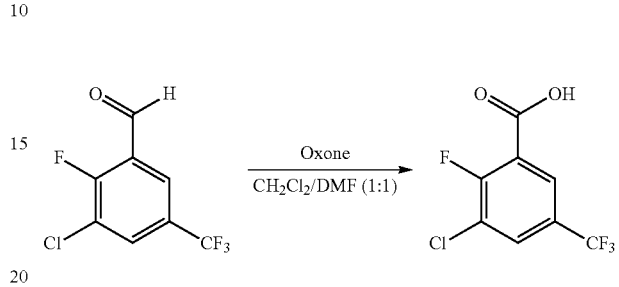

To a solution of 3-chloro-2-fluoro-5-trifluoromethyl-benzaldehyde (4.2 g, 18.5 mmol) in DMF (21 ml) and CH₂Cl₂ (21 ml) was added potassium peroxomonosulfate (11.4 g, 18.5 mmol, 1.0 equiv.) whereupon the temperature rose from 25 to 34° C. The white suspension was stirred for 2 h, the white solid was filtered off, the filter cake was washed with CH₂Cl₂ (25 ml) and the solvent was removed under vacuum. The obtained residue was dissolved in TBME (50 ml) and the pH was adjusted to 14 upon addition of NaOH (2M, 22.7 ml, 45.4 mmol, 2.45 equiv.). The aqueous phase was separated, washed with TBME (25 ml), whereas the organic phases were washed with water (25 ml). The combined aqueous phases were acidified upon addition of HCl (37%, 8.4 ml, 5.35 equiv.) and extracted with TBME (50 ml). The organic phase was washed three times with brine (75 ml), whereas the aqueous phases were washed with TBME (25 ml). The combined organic phases were dried over sodium sulfate, which was filtered off, washed with TBME (20 ml) and the solvents were removed under vacuum to yield the 3-chloro-2-fluoro-5-trifluoromethyl benzoic acid as white solid (4.2 g of crude product, 93.4% yield). The crude product was dissolved in hot methyl cyclohexane (20 ml), the oil bath was removed and the suspension was slowly cooled to ambient temperature, whereupon white crystals precipitated. The white suspension was stirred in an ice bath for 2 h, the crystals were filtered off, washed with methyl cyclohexane (5 ml) and dried under vacuum until weight constancy to yield the title compound as white crystals (3.1 g, 68.9% yield).

Example 3.6

Synthesis of 3-chloro-2-fluoro-5-trifluoromethyl benzoic acid

Oxidation with Potassium Permanganate

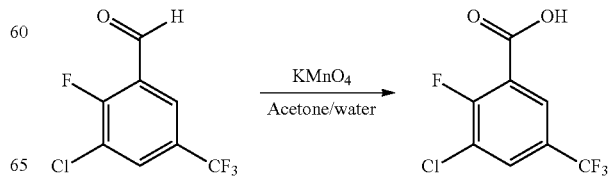

To a solution of 3-chloro-2-fluoro-5-trifluoromethyl-benzaldehyde (1.0 g, 4.41 mmol) in acetone (15 ml) and water (3 ml) was added potassium permanganate (0.837 g, 5.3 mmol, 1.2 equiv.) and the corresponding dark violet reaction mixture was stirred for 30 min to achieve full conversion. The solvents were removed under vacuum and the dark suspension was quenched upon addition of sodium sulfite solution (sat., 20 ml). The dark violet solid was filtered off and washed with water (10 ml). The turbid light brown mother liquor was treated with HCl (25%, 3 ml, 92.3 mmol, 20.9 equiv) adjusting the pH to 1 and $CH_2Cl_2$ (50 ml) was added. The phases were separated, the organic phase was washed with water (20 ml), whereas the aqueous phase was washed with $CH_2Cl_2$ (20 ml). The combined organic phases were dried over sodium sulfate, filtered and the solvent was exchanged under vacuum with methyl cyclohexane (35 ml). The turbid suspension was concentrated under vacuum, the white precipitate was filtered off and the crystals were dried under vacuum until weight constancy to yield the product as white crystals (1.02 g, 93.8% yield).

Example 3.7

Synthesis of 3-chloro-2-fluoro-5-trifluoromethyl benzoic acid

Deprotonation, $CO_2$ as Electrophile

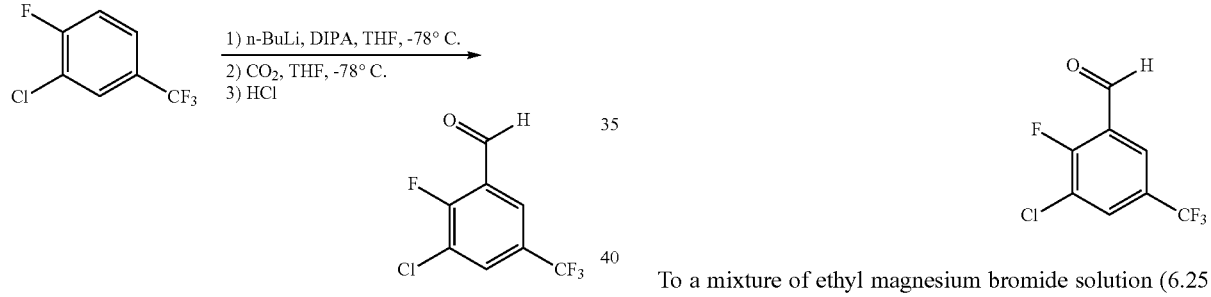

To a solution of diisopropyl amine (19.79 ml, 140 mmol, 1.4 equiv.) in 100 ml THF was added at −78° C. n-BuLi (1.6 M in hexane, 81.25 ml, 130 mmol, 1.3 equiv.) within 25 min, the light yellow solution was stirred for 30 min at −78° C. and a solution of 3-chloro-4-fluoro benzotrifluoride (19.86 g, 100 mmol, 1 equiv.) in 100 ml of THF was added dropwise within 25 min keeping the temperature between −73 and −76° C. The resulting yellow solution was stirred for 1 h at −78° C., transferred into an addition funnel which was cooled with an acetone/dry ice mixture and added to a cold (−78° C.) mixture of $CO_2$ (44.0 g, 1000 mmol, 10 equiv.) in 100 ml of THF within 1 h keeping the temperature between −75 and −78° C. Afterwards the reaction mixture was transferred into an addition funnel and added to a solution of HCl (aq., 2M, 163 ml) within 15 min at −4° C., stirred for 15 min and transferred into a separation funnel. After separation of the phases, the aqueous phase was extracted with TBME (300 ml), the combined organic phases were dried over sodium sulfate (370 g), filtered with suction on funnel with a fritted disk, washed with TBME (100 ml in total) and the TBME was removed under vacuum to yield a light yellow solid (23.48 g of crude product, 96.8% yield). The crude product was treated with methyl cyclohexane (117 ml) and heated in a pre-heated oil bath to reflux. After 5 min, a brown clear solution was obtained, the oil bath was removed, the reaction mixture was cooled to ambient temperature, seeding crystals (2 mg) were added and the mixture was stirred overnight at ambient temperature. After 17 h the off-white suspension was stirred in an ice bath (0-5° C.) for two hours, the obtained crystals were filtered off, the crystals were washed with cold methyl cyclohexane (39 ml) and the crystals were dried until weight constancy to yield the product as white crystals (18.75 g, 77.3% yield).

Example 3.8

Synthesis of 3-chloro-2-fluoro-5-trifluoromethyl benzoic acid

Grignard, $CO_2$ as Electrophile

To a mixture of ethyl magnesium bromide solution (6.25 ml, 6.25 mmol, 1.25 equiv., 1M in THF) and diisopropyl amine (77.7 µl, 0.5 mmol, 0.1 equiv.) was added 3-chloro-4-fluoro-benzo trifluoride (0.99 g, 5 mmol in THF (2 ml)) at ambient temperature and the mixture was heated in an oil bath to 50° C. for 13 h. The brown clear reaction mixture was cooled to 0-5° C., was transferred into a syringe and added dropwise to a solution of $CO_2$ (2.2 g, 50 mmol, 10 equiv.) in THF (5 ml) at −70° C. and stirred for 15 min. To the brown suspension was added HCl (1M, 14 ml) and the phases were separated. The aqueous phase was extracted with TBME (10 ml), the combined organic phases were dried over sodium sulfate, filtered, washed with TBME and the solvents were removed under vacuum to yield a dark brown oil (0.97 g of the crude product). The crude product was treated with methyl cyclohexane (4.4 ml) and heated in a pre-heated oil bath to reflux. After 5 min, a brown clear solution was obtained, the oil bath was removed, the reaction mixture was cooled to ambient temperature and the formed suspension was stirred overnight at ambient temperature. After 18 h the brown suspension was stirred in an ice bath (0-5° C.) for two hours, the obtained crystals were filtered off, the crystals were washed with cold methyl cyclohexane (1.6 ml) and the crystals were dried until weight constancy to yield the product as white crystals (0.46 g, 38.2% yield).

Example 3.9

Synthesis of 3-chloro-2-fluoro-5-trifluoromethyl-benzoate dicyclohexyl-ammonium

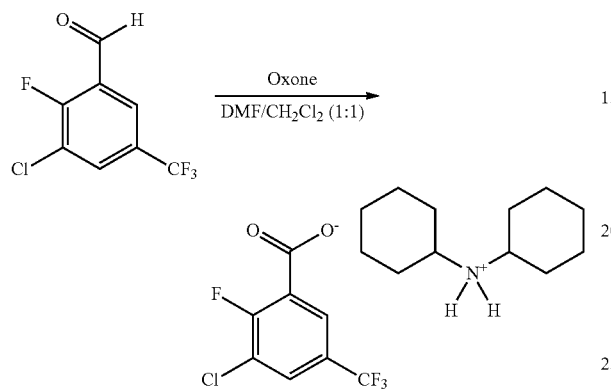

Example 3.10

Telescoped process for the preparation of 3-chloro-2-fluoro-5-trifluoromethyl benzoic acid

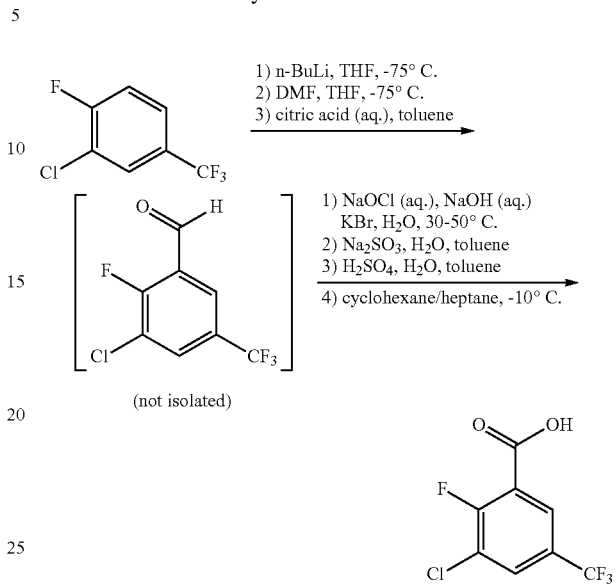

To a solution of 3-chloro-2-fluoro-5-trifluoromethyl-benzaldehyde (23.0 g, 101.5 mmol) in DMF (110 ml) and CH$_2$Cl$_2$ (110 ml) was added potassium peroxomonosulfate (62.4 g, 101.5 mmol, 1.0 equiv.) whereupon the temperature rose from 25 to 34° C. The white suspension was stirred for 2.5 h, the white solid was filtered off, the filter cake was washed with CH$_2$Cl$_2$ (50 ml) and the solvent was removed under vacuum. The obtained residue was dissolved in TBME (240 ml) and the pH was adjusted to 14 upon addition of NaOH (2M, 101.5 ml, 203.0 mmol, 2.0 equiv.). The aqueous phase was separated, washed with TBME (75 ml), whereas the organic phases were washed with water (75 ml). The combined aqueous phases were acidified upon addition of HCl (25%, 52.8 ml, 4.0 equiv.) and extracted with TBME (200 ml). The organic phase was washed three times with brine, whereas the aqueous phases were washed with TBME (100 ml). The combined organic phases were dried over sodium sulfate, which was filtered off, washed with TBME (50 ml) and the solvents were removed under vacuum to yield the 3-chloro-2-fluoro-5-trifluoromethyl benzoic acid as white solid (21.35 g of crude product, 86.7% yield). The crude product was dissolved in hot acetone (200 ml) and dicyclohexyl diamine (17.5 ml, 88 mmol, 1.0 equiv.) was added at reflux temperature and the mixture was stirred for 20 min, whereupon white crystals precipitated. The oil bath was removed, the suspension was slowly cooled to ambient temperature, the crystals were filtered off, washed with acetone (60 ml) and dried under vacuum until weight constancy to yield the title compound as white crystals (35.8 g, 83.2% yield). MS (EI): acid: m/z 241.0 ([M−H]$^-$, 100%), amine: m/z 182.0 ([M+H]$^+$, 100%). $^1$H-NMR (CDCl$_3$, 400 MHz): δ 9.57 (br s, 2H), 7.96 (dd, 1H), 7.64 (dd, 1H), 3.07 (m, 2H), 2.09 (m, 4H), 1.81 (m, 4H), 1.65 (m, 2H), 1.58-1.40 (m, 4H), 1.35-1.05 (m, 6H).

To a solution of 3-chloro-4-fluoro-benzotrifluoride (59.9 g, 0.302 mol) in THF (350 ml) was added dropwise at −73 to −80° C. 200 ml of n-BuLi (1.6 M in hexanes; 200 ml, 0.32 mol, 1.06 equiv.) within 1 hour. The clear yellow solution was stirred for 30 min at −75° C. and a solution of DMF (24.5 g, 0.335 mol, 1.11 equiv.) in THF (100 ml) was then added dropwise within 30 minutes at −74 to −78° C. The slightly yellow reaction mixture was stirred for 1 h at −75° C. and was then warmed to 0° C. and quenched at this temperature by dropwise addition of aqueous citric acid solution (30%, 300 ml). The resulting biphasic mixture was warmed to 20 to 25° C. and the layers were then allowed to separate. The lower aqueous layer was removed and the organic layer diluted with toluene (300 ml) and then washed with water (200 ml). The organic layer was concentrated under reduced pressure and with a jacket temperature of 60° C. to yield 85.2 g of a slightly yellow oil with an aldehyde content of ~76% (w/w) (according to $^1$H NMR). This oil was then added within 30 to 60 minutes at 30 to 50° C. to a stirred solution of sodium hypochlorite (10% in H$_2$O; 230 g, 0.309 mol), potassium bromide (31.8 g, 0.266 mol) and sodium hydroxide (28% in H$_2$O; 92 g, 0.644 mol) in water (220 ml). The resulting mixture was cooled to 20-25° C. and then quenched by addition of aqueous sodium sulfite solution (32 g Na$_2$SO$_3$ in 355 ml water). The mixture was treated with toluene (350 ml) and the biphasic mixture stirred for 10 minutes. The lower product-containing aqueous layer was separated and washed with toluene (350 ml). The aqueous layer was acidified to pH 2 using sulfuric acid (20% in H$_2$O; 240 g) and then extracted with toluene (450 ml). From the organic layer toluene was completely distilled off under reduced pressure. The residue (59 g) was dissolved at reflux temperature in a mixture of cyclohexane (141 ml) and heptane (141 ml). The clear solution was then cooled to −10° C. within 6 hours whereupon crystals precipitated. The crystals were filtered off, washed with cyclohexane/heptane 1:1 and dried at 50° C. and 30 mbars over night to yield the title compound as colorless crystals (55.8 g, 76% yield) with a purity of 100% (HPLC, area %).

The invention claimed is:

1. A process for the preparation of 3-chloro-2-fluoro-5-trifluoromethyl benzoic acid of the formula

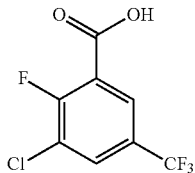
I or of a salt thereof, comprising the steps of
a) transforming the 3-chloro-4-fluoro-benzo trifluoride of formula II,

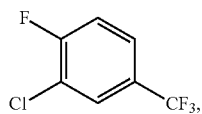
II into the 3-chloro-2-fluoro-5-trifluoromethyl benzaldehyde of formula III,

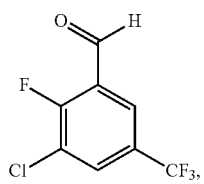
III and b) oxidizing the 3-chloro-2-fluoro-5-trifluoromethyl benzaldehyde with an oxidant to form the 3-chloro-2-fluoro-5-trifluoromethyl benzoic acid of formula I or of a salt thereof.

2. The process of claim 1, wherein the transformation into the 3-chloro-2-fluoro-5-trifluoromethyl benzaldehyde of the formula III is performed by deprotonating the 3-chloro-4-fluoro-benzo trifluoride with a metalorganic base followed by adding an electrophile in an organic solvent at a reaction temperature of −100° C. to 25° C.

3. The process of claim 2, wherein a protic acid as quenching agent is added subsequent to the deprotonation and subsequent to the addition of the electrophile.

4. The process of claim 2, wherein the metalorganic base is selected from n-butyl lithium, and lithium diisopropylamide.

5. The process of claim 2, wherein the electrophile is selected from an N,N-dialkylformamide, an N,N-diarylformamide or an N-alkoxy-N-alkyl formamide.

6. The process of claim 1, wherein the oxidant is selected from alkali- or alkali earth hypochlorites, -hypobromites, -chlorites, -chlorates, -persulfates or -permanaganates.

7. The process of claim 6, wherein the reaction is performed in the presence of an alkali hydroxide base and an alkali bromide in an aqueous solvent at a reaction temperature of 10° C. to 100° C.

8. The process of claim 1, wherein the 3-chloro-2-fluoro-5-trifluoromethyl benzaldehyde of the formula III is not isolated prior to the oxidation in step $b_2$).

* * * * *